(12) United States Patent
Durette

(10) Patent No.: US 6,681,771 B2
(45) Date of Patent: Jan. 27, 2004

(54) ORGAN SHIELDS FOR MEDICAL PROCEDURES

(76) Inventor: Jean-Francois Durette, 1170 East Henri-Bourassa Blvd., Montreal, Quebec (CA), H2C 1G4

( * ) Notice: Subject to any disclaimer, the term of this patent is extended or adjusted under 35 U.S.C. 154(b) by 0 days.

(21) Appl. No.: 10/063,121

(22) Filed: Mar. 22, 2002

(65) Prior Publication Data

US 2003/0178028 A1 Sep. 25, 2003

(51) Int. Cl.⁷ .................................................. A61C 5/14
(52) U.S. Cl. ........................ 128/859; 128/842; 128/861
(58) Field of Search ................................. 128/848, 846, 128/857, 858, 859–862; 2/9, 15

(56) References Cited

U.S. PATENT DOCUMENTS

| 4,223,229 A | 9/1980 | Persico et al. | |
|---|---|---|---|
| 4,601,286 A | 7/1986 | Kaufman | |
| 4,745,916 A | * 5/1988 | Seber | 128/155 |
| 4,790,031 A | * 12/1988 | Duerer | 2/15 |
| 4,977,904 A | 12/1990 | Kaufman | |
| 5,669,395 A | * 9/1997 | Thompson | 128/846 |
| 5,717,992 A | * 2/1998 | Tilghman | 2/9 |
| 5,993,439 A | 11/1999 | Costello et al. | |
| 6,278,601 B1 | * 8/2001 | Price | 361/272 |

FOREIGN PATENT DOCUMENTS

| EP | 0 574 226 | 12/1993 |
|---|---|---|
| GB | 957 594 | 5/1964 |
| WO | WO 98 01865 A | 1/1998 |

* cited by examiner

*Primary Examiner*—Michael A. Brown
(74) *Attorney, Agent, or Firm*—Ryan N. Carter

(57) ABSTRACT

Shields for protecting parts of the body during use of lasers or similar high intensity light. One of the shields is a dental shield shaped to conform to the typical dental alignment in the buccal area of the patient. Other shields are for protecting the genital areas of either a male or female patient. The female shield protects the vulva of a female patient. The male genital shield is a penile guard, in the form of a thick tube that is placed around the upper half of the penis when a procedure is performed for removing the hair follicles on the lower half part of the penis. The shields are made of a light color, preferably white, in order to disperse or reflect the energy and avoid the penetration of the laser or other light instruments all the way through the material.

6 Claims, 3 Drawing Sheets

ORGAN SHIELDS FOR MEDICAL PROCEDURES

BACKGROUND OF INVENTION

Lasers, especially diode lasers, are sometimes used to remove unwanted hair from various parts of the body, including hair on the upper lip and in areas around the genitals of a male or female patient, including the so-called bikini line. When used to remove hair from the upper lip, these hair removal lasers may cause pain in the patient's teeth and gums particularly at the site of fillings in the teeth. This is principally caused by what is typically referred to as acoustic resonance. In addition, some lasers, such as the $CO_2$ laser can make a permanent black spot on the teeth if the laser is directed at the teeth. It may even make a crack in the teeth. Moreover, it is not known what the potential affect of the hair removal laser may be on the minute blood vessels in tissue and organs in the area surrounding where the hair is being removed as well as in the gums and pulp within the roots of the teeth. This is especially true of the diode and Nd:Yag as they penetrate deeper than other lasers. Although these adverse effects are undocumented, they are a matter of concern to surgeons. Since removal of unwanted hair on the upper lip and other areas of the body is a desired but elective technique for women and sometimes men, there is a need for some means of protecting the patient's organs, teeth and gums from the potential adverse affects of lasers when used for hair removal. In addition, there are other medical devices such as instruments that transmit intense light used in medical procedures. Any medical instrument, including those with a cooling apparatus such as a cooling ring, which presses the lips against the teeth and gums will benefit from the invention.

SUMMARY OF INVENTION

The devices of the invention include a mouth guard or dental shield shaped to conform to the typical dental alignment in the buccal area of the patient, being worn over the teeth behind the lips in the buccal area. The invention also includes both a male and a female genital shield that serve the same purpose as the dental guard, except they protect the genital areas of the patient. The female shield protects the vulva of a female patient, i.e., the delicate membrane of the vaginal and urethral openings, the labia minora and all other very sensitive parts of the female genital area. The genital shield is held in place by and behind the labia majora, and will fit most patients by positioning the shield so that the vermilian border (the junction of the mucosal membrane and skin) is well placed. The male genital device is a penile guard, in the form of a thick tube that is placed around the upper half of the penis when a procedure is performed for removing the hair follicles on the lower half part of the penis. The devices of the invention are preferably made of a soft rubbery polymer so as to conform more easily to the individual patient's features. The shields are made of a light color, preferably white, in order to disperse or reflect the energy and avoid the penetration of the laser or other light instruments all the way through the material.

DETAILED DESCRIPTION

Figure 1:
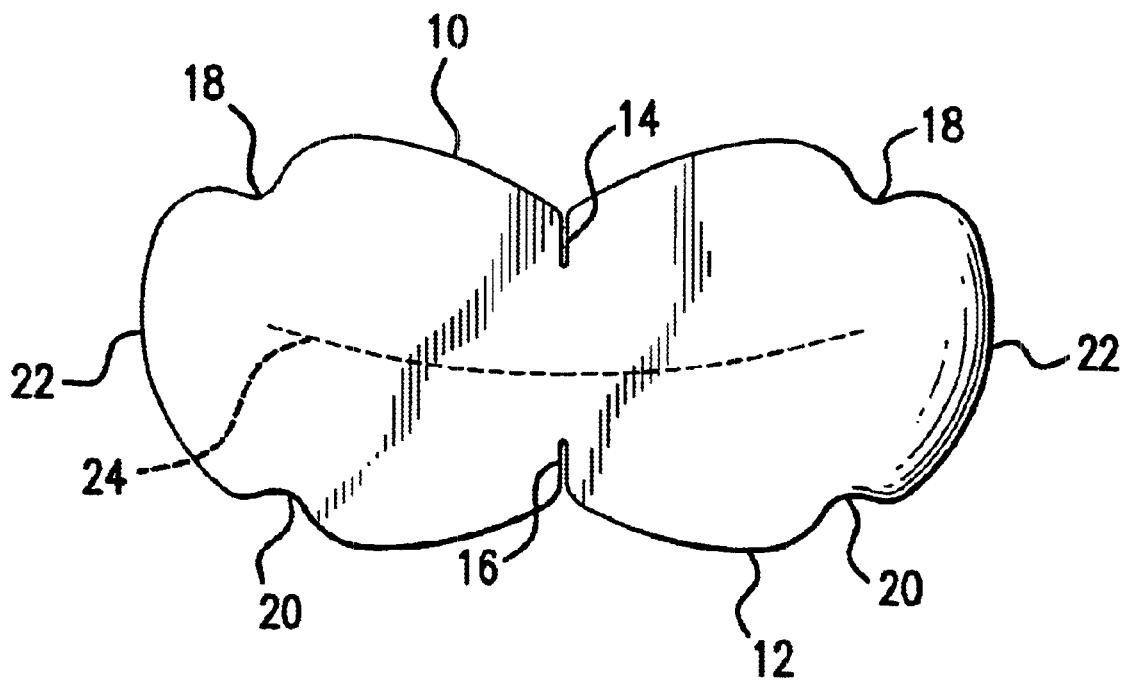
FIG. 1 is a plan view of a dental shield made according to the principles of the invention and showing the shield before it is bent to conform to the patient's teeth.
Figure 2:
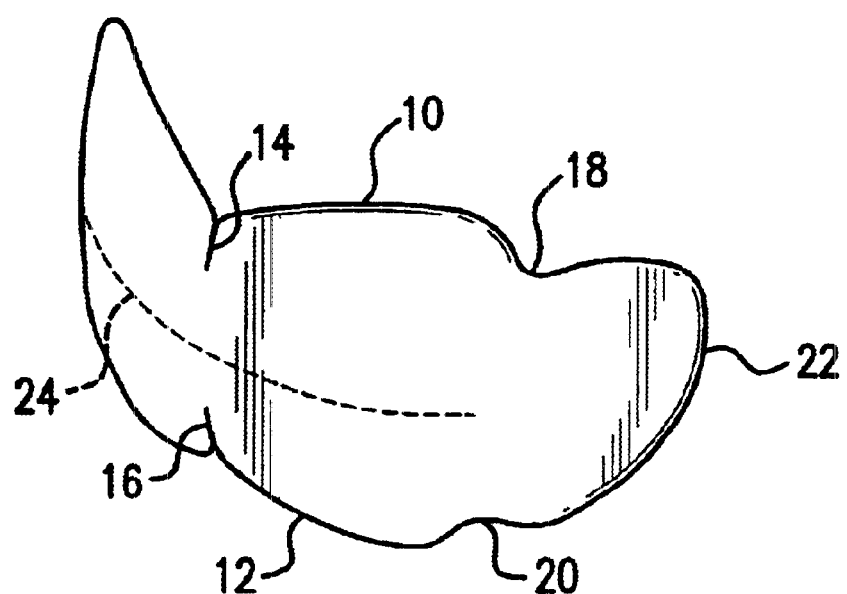
FIG. 2 is a perspective view of the shield of FIG. 1.

Referring first to FIGS. 1 and 2, there is shown a device constructed according to the principles of the invention for use as a mouth guard or dental shield for protecting the patient's teeth and gums when medical lasers or other devices are being used around the area of the patient's mouth to remove, for example, unwanted hair, port wine stains or veins, wrinkles etc. As best seen in FIG. 1 which is a plan view of the shield of the invention, the shield comprising a main body having a top edge 10 and a bottom edge 12, each of which is an irregularly shaped edge that conforms to the typical dental alignment in the buccal area of the patient between the teeth and the lips. The typical buccal anatomy requires that the top edge 10 and bottom edge 12 be provided with notches 14 and 16 at approximately the center of the shield. Also, spaced from the central notches 14 and 16 are side notches 18 along the top edge 10 and side notches 20 along the bottom edge 12. When the shield is in place in the mouth of the patient, the notches 20 along the bottom edge 12 are more anterior than the side notches 18 along the top edge 10. The ends 22 of the shield are more rounded at the lower aspects giving the shield ends 22 a more upward slanting appearance. The central notches 14 and 16 are provided to be comfortable for the patient since in some patients the central adhesion is quite close to the teeth while in others the adhesion is farther away. Also, all patients have centrally located bumps and bumps on the lateral aspects.

The shield is preferably of a thickness between 2 mm and 6 mm, with the thicker shield being preferred. However, the shield may be thicker at the top portion to add protection and absorption of the pressing energy or a cooling device, and thinner at the bottom, to be more malleable and easy to place more comfortably. Very few procedures are done inferiorly as the mustache is over the upper lip and is the area where most hair removal is performed. Nonetheless, the shield may be of substantially the same thickness throughout, especially when used on men who may want to have all their beard removed and need as much protection on the lower lip as on the upper lip.

As indicated above, some patients have their central adhesion quite close to the teeth and some have it farther away. Those who have it farther away will be less protected as the notch 14 will have less material. The doctor or technician has the option to cut the notch slightly so that it is increased for more comfort. If the patient is comfortable without increasing the notch, then the patient will be better protected by the intact rubber mass within the notch. With the dental shield of the invention, it is not important that the patient be able to close his or her mouth and have the teeth touch. But it is important that the patient close the mouth a sufficient amount to fill the buccal area while still being comfortable.

The shield may have an optional central opening 24 to provide an air passage for breathing. Opening 24 may be identified by imprinting or otherwise forming dotted lines on the shield so as to aid the specialist in cutting an opening or the opening may be precut during the manufacturing process.

Figure 3:
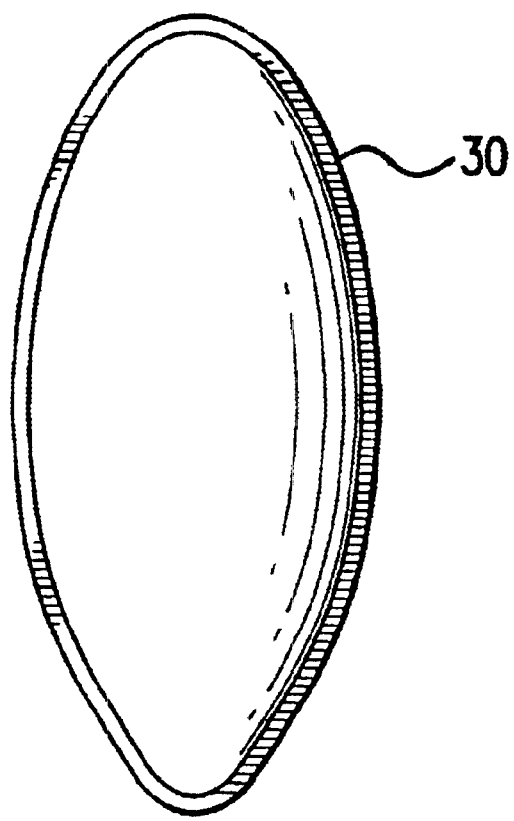
FIG. 3 is a top view of a second embodiment of a shield of the invention adapted for protecting the female genital area.
Figure 4:
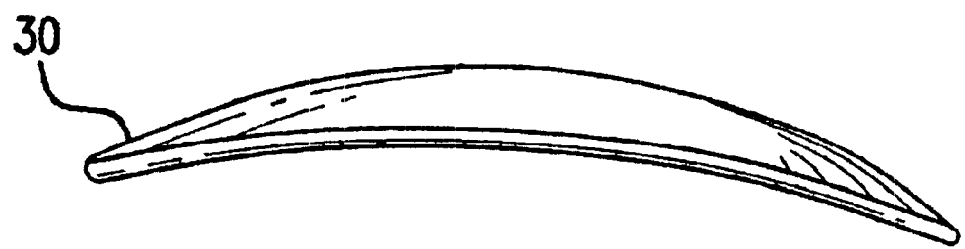
FIG. 4 is a side view of the second embodiment of the invention.
Figure 5:
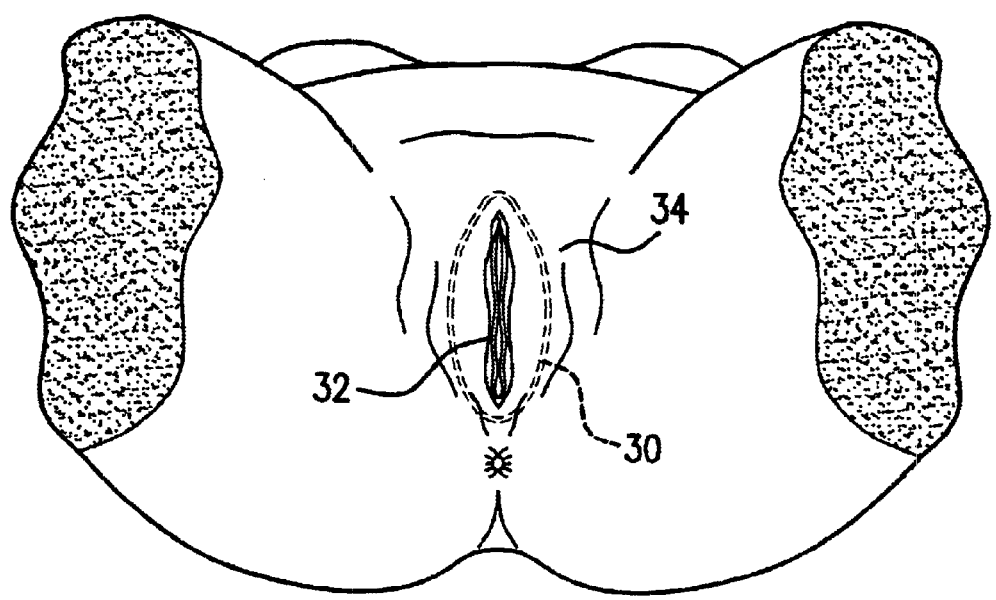
FIG. 5 is an illustration of the female genital area showing placement in dotted lines placement of the shield of FIGS. 3 and 4.

Referring now to the embodiment of FIGS. 3, 4 and 5, there is shown a shield 30 for use in protecting the female genital area. The shield of this embodiment serves the same function in the same way as the dental shield of the first embodiment, except it protects the female genital area, i.e., the vulva and the delicate membrane of the vaginal and urethral openings, the labia minora and all other (very sensitive) elements. The shield is generally dome shaped in the form of an oval so that it will more easily fit between the labia minora 32 and the labia majora 34 with the shield 30 positioned behind and held in place by the labia majora 34. The shield 30 is shown in dotted lines in FIG. 5. The installation of the shield 30 can be performed by the patient herself or the technician, but must be verified by the technician. The presence of the shield 30 behind the labia majora 34 enables the technician to stretch the labia majora 34 in order to expose the hair that is to be removed by lasing the hair follicles.

The dome shape of the shield 30 is to accommodate the bulging that may exist because of the difference between the anatomies of females, especially on the upper aspect of the genital area, where some patients have a larger clitoris or labia minora. This dome shape thus minimizes the possibility of the shield 30 inadvertently coming loose during a procedure. The shield 30 is preferably made substantially the same thickness, although the center may be slightly thicker with the edges feathered to improve flexibility for an optimum fit on the anatomy of different patients. With this shape and construction, the shield will fit most patients so that the vermilian border (the junction of the mucosal membrane and skin) is well placed.

The removal of the hair present on the vulva is usually (but not exclusively) the object of the laser treatment. For those patients who wish to have all of the hair follicles removed, it becomes a delicate procedure for the technician, mainly because of the danger of hurting and/or burning the mucous membrane of any part of the vulva. Some females have hair even inside the labia majora and it will be up to the technician to lase these while manually positioning the shield 30 to allow lasing while still protecting the other parts of the mucosal tissue.

Figure 6:
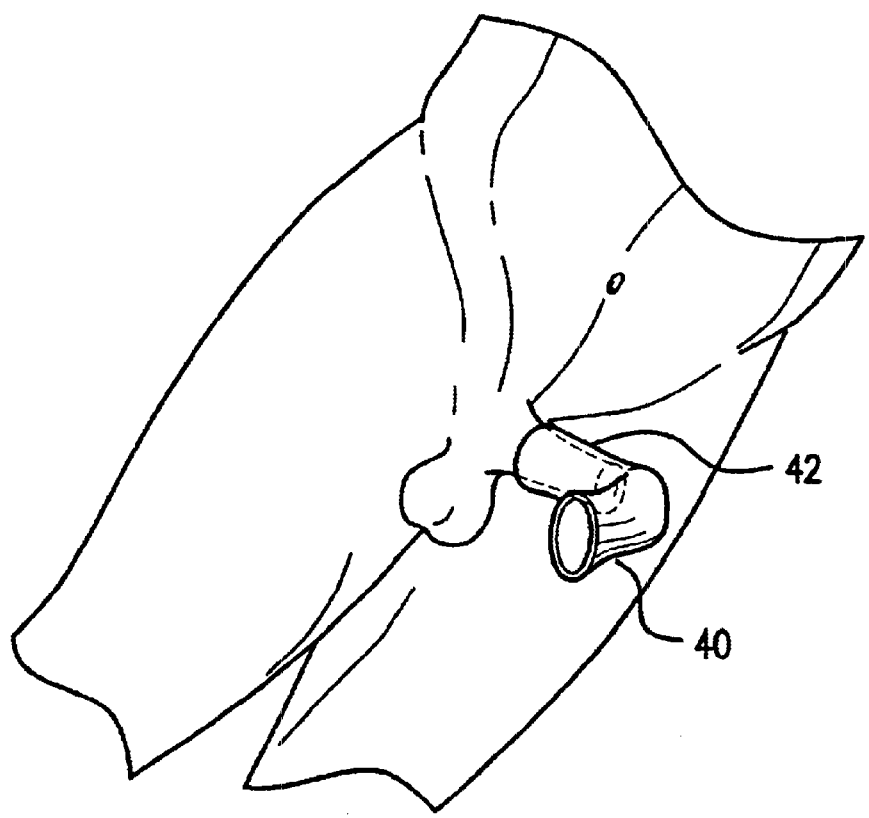
FIG. 6 is an illustration showing the third embodiment of the invention adapted for protection of the male organ.

Referring now to the embodiment of FIG. 6, there is shown a shield 40 that serves as a penile laser guard where hair is to be removed from the male genital area. The shield 40 is comprised of a thick tube made of the same flexible material described herein for the dental shield and the female genital shield 30. The shield 40 is shaped to be placed around the upper half of the penis 42 during a procedure for removing the hair follicles on the lower half part of the penis 42.

The shields of the embodiments of the invention are made of a soft rubbery polymer, such as an elastomer, to provide for a better and more comfortable fit regardless of the individual features of the patient. Although one size may be made to accommodate most patients, it may be desirable to make each shield in more than one size. The material used for the shields may be selected from a variety of polymers. Some polymers are very soft and easy to compress and will conform very easily to each patient's anatomy. Other materials may be more or less porous while still others may be less resistant to heat and thus suitable for autoclaving purposes. Therefore, if the shield is to be used repeatedly after cleaning and sterilizing, a suitable polymer should be chosen for the material. If the shield is to be marketed for a single patient use and then disposed of, it may be offered clean, non-sterile or sterile. On the other hand, if the shield is to be marketed for single use, it could be packaged in a sterile condition and then disposed of after use.

In addition to blocking lasers and high light energy, the rubbery nature of the shield serves as a cushion to alleviate pain from pressing devices used to treat the patient. The mere presence of a rubber shield can actually decrease pain from the pressing laser, energy and/or cooling device before the energy is applied.

The shield is preferably colored in order to disperse, reflect and block penetration of laser or other high intensity light sources. Although other colors or transparent material will serve to block various lasers, the lighter colors, especially white, will block most of the diode laser light, blocking approximately 99% of such laser light. If the shield is made entirely black, this will block 100% of all diode laser light, but the material will absorb and may melt instead of reflecting the light. The color of the shield will be selected depending upon the particular laser being used. If a laser is directed onto the shield long enough, which would be abnormal usage, the material that forms the shield may heat up if it is a dark color, and damage would occur not only to the shield but also to the patient who may get burned by the heated material. Since these shields are used on areas of the body that are very sensitive, it is important that excessive heating of the shield not occur. White is the preferred color, and it works also with an intense pulse light energy, which although not a laser, is a softer, but still high intensity energy source.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is:

1. A shield for protecting sensitive parts of a patient's body near where high intensity light energy is being applied by a practitioner in a procedure to remove unwanted characteristics of the patient's skin, said shield comprising: a main body shaped and adapted to be positioned so as to cover the area of the patient's anatomy to be protected, the main body being made of a soft rubbery polymer so as to conform more easily to the individual patient's anatomy, and the material that forms the main body being made of a color that will disperse and reflect the light energy being applied so as to prevent penetration of the light energy completely through the material to the sensitive part of the patient's anatomy covered by the main body; the main body being shaped to conform to the buccal area anteriorly to a patient's teeth for protection of a patient's teeth and gums, the main body having a top edge and a bottom edge joined by rounded outer ends, the top edge and bottom edges each having a central notch, the top and bottom edges also having side notches spaced outwardly from the central notches, and the areas between the rounded ends and the outer notches in the bottom edge being less round than the corresponding areas between the rounded ends and the top edge.

2. The shield of claim 1 in which the main body has a central opening to provide an air passage for the patient to breathe.

3. The shield of claim 1 in which the main body is formed with indicator lines at the ends of the shields to guide the practitioner in decreasing the length of the shield if necessary, when used in patients with a smaller mouth.

4. The shield of claim 1 n which the central notches in the upper and lower edges of the main body are substantially filled with the polymer material that comprises the main body but are capable of being deepened as needed by the practitioner so as to conform to the personal features of each patient while covering as much as possible of the gums of the patient.

5. The shield of claim 1 in which the material of the shield is a light color that will block substantially all the light energy being applied by the practitioner.

6. The shield of claim 5 in which the color of the material is white.

* * * * *